United States Patent

Brajnovic et al.

[11] Patent Number: 5,286,196
[45] Date of Patent: Feb. 15, 1994

[54] SYSTEM INDIVIDUALLY ADAPTABLE TO ELEMENTS IMPLANTED IN THE DENTINE AND THE LIKE

[75] Inventors: Isidor Brajnovic, Gothenberg; Stig Wennberg, Angered, both of Sweden

[73] Assignee: Nobelpharma AB, Gothenborg, Sweden

[21] Appl. No.: 842,323

[22] Filed: Feb. 28, 1992

[30] Foreign Application Priority Data

Mar. 1, 1991 [SE] Sweden .................................. 9100603

[51] Int. Cl.$^5$ .............................................. A61C 8/00
[52] U.S. Cl. .................................... 433/173; 433/172
[58] Field of Search ............... 433/167, 172, 173, 190, 433/196, 215, 229

[56] References Cited

U.S. PATENT DOCUMENTS

| | | | |
|---|---|---|---|
| 3,435,526 | 4/1969 | Brancato. | |
| 3,748,739 | 7/1973 | Thilbert | 433/173 |
| 4,645,453 | 2/1987 | Niznick. | |
| 5,052,928 | 10/1991 | Andersson | 433/172 |
| 5,057,017 | 10/1991 | Sillard | 433/172 |
| 5,064,374 | 11/1991 | Lundgren | 433/173 |

Primary Examiner—Gene Mancene
Assistant Examiner—Nicholas D. Lucchesi
Attorney, Agent, or Firm—Pollock, Vande Sande & Priddy

[57] ABSTRACT

A bridge system which is individually adapted to elements implanted in dentine, joints, or the like and/or to parts secured in the implanted elements, comprises at least two module units which are attachable to the implanted elements or parts and have first surfaces for attachment to the elements and second surfaces separate from the first surfaces, and an elongate, curved member which is securable in the module units at the second surfaces. The elongate, curved member is designated with a profile and made of a material having a quality of titanium and a tissue affinity equivalent to that of titanium. The profile of the elongate member is designed in its cross-section with a plane underside adapted to be applied against the second surfaces and with elements projecting from the underside to facilitate holding of a prosthesis part (tooth/tooth part), abutment or the like which is being secured in the bridge, the material and the profile permitting bending without essentially impairing the strength of the elongate element in the bridge.

13 Claims, 5 Drawing Sheets

SYSTEM INDIVIDUALLY ADAPTABLE TO ELEMENTS IMPLANTED IN THE DENTINE AND THE LIKE

TECHNICAL FIELD

The present invention relates to a bridge system which is individually adapted to elements implanted in the dentine, joints and the like and/or to parts secured in the implanted elements. The bridge in this case is of the type which is made up of, on the one hand, two or more module units which can be attached to the elements or parts and which have further surfaces separate from the surfaces (second surfaces) of attachment to the elements or parts (first surface), and, on the other hand, an elongate, curved element such as a rail which is secured/can be secured in the module units at or on the second surfaces. Present invention also relates to a method using models of dentine, jaw, joint and, which have dummies or attachment positions for elements implanted in the dentine, jaw, joint and the like and/or parts secured to the elements, to produce the individually adapted bridge with the aid of two or more module elements and the said elongate, flexible element (rail).

BACKGROUND OF THE INVENTION

It is already known to use different module units in the construction of dental bridges. The module units are in this case available in a number of variants, and a number of module units are chosen to form part of the bridge being constructed. It is also already known to use curved, beam-shaped elements which are connected to the "free" end surfaces after these have been ground to form a common plane, to which the curved element or the beam has been applied. The bridge produced in this way is intended to constitute a structure for supporting the actual prosthesis, abutment, and the like.

In bridges of these types it is particularly desirable to use titanium which has affinity for tissue. Characteristic features of this material are its hardness and the fact that it is comparatively brittle. This has meant that it has been necessary to cast the elongate, flexible element or rail. The product of cast, curved rails imposes considerable demands on the casting method. It has proven difficulty to obtain cast, elongate and curved elements having the strength which is required in this connection. It is not possible to leave the casting to a less individual working by a dentist or dental technician and in so doing obtain satisfactory results from the stability point of view of. The method of casting the curved elements/rails also has the disadvantage that it is difficult to make adjustments, during and after casting, to the curved shape of the elongate element/rail.

The present invention aims to solve these problems and proposes a method of producing the curved element/rail in which the latter is bent in a bending tool. However, this entails other requirements on account of the brittleness of the material. In the present invention method it is important to obtain the curved or bent shape without causing substantial deterioration from the point of view of its strength. There is also a requirement for devices and methods which are simplified from all manufacturing aspects and which are easy to use and carry out, respectively, by practising dentists or dental technicians. Manufacture should also be possible with a high prescribed degree of accuracy (1/100 mm).

SUMMARY OF THE INVENTION

The feature which may chiefly be regarded as characterizing the new bridge system according to the present is the fact that the elongate, curved element or rail is designed with a profile and with a quality of titanium or another had metal, composite, and the like, and with a tissue affinity equivalent to that of titanium, which permits bending without essentially impairing the strength of the element in the bridge. A further characteristic feature is that the profile is also designed to perform part of a holding function for prosthesis parts, abutments, and the like which are secured in the bridge.

In the embodiment of the present invention the elongate, flexible element/rail is given a profile of unique cross-section. This includes first and second lateral surfaces which merge via recesses into a common top part which is slightly offset in the profile's cross-section in the direction towards the first lateral surface. The first lateral surface has a length which is shorter than the second lateral surface. The first lateral surface (its top edge forms an inside surface/inside radius in the curved shape of the rail, and the plane underside of the profile can be made to bear against the further surfaces of the module units over a widespread bearing area. The recesses in the cross-section form anchoring steps for retention of means which are incorporated for retention the actual prosthesis part, tooth, tooth part, support part and the like on the bridge and the elongate, curved elements or rail.

The titanium material is factory-made with exact material properties and is supplied in bar form in predetermined, optionally cut lengths. In the present case it is therefore important for a quality of titanium to be chosen which withstands the bending without any deterioration in strength. It has been found in this respect that the titanium material quality should have a modulus of elasticity in the range of 100–120, and preferably about 110.

According to the present invention, the external shapes of the module units are carefully tested so as to permit the construction of a very large number of unique bridge structures. Despite this, the number of module units chosen is relatively small. For example, the number of module units can be between 5 and 15. In a preferred embodiment, the number of module units is about 10. Each module unit has a securing part by means of which the module unit is secured in one of the implanted elements and/or on the part secured in the element. In addition, each module unit also has a part which bears one of the second surfaces. The section which bears the second surface is here called the first section, and the section which bears the securing part is called the second section. Identical module units can be incorporated together, or differing module units can be incorporated complementing one another, in one and the same titanium bridge. The positions and inclinations of the implanted elements in the dentine, for example, vary greatly on an individual basis, since the implantation must be carried out in accordance with the dentine in question. The aim of selecting and assembling the module units is to ensure that their second surfaces will form a common plane to which it will be possible to apply the curved element/rail via its plane underside. On account of the different inclinations of the implanted elements or their parts, the module units have to be worked, for example ground, in order to form the common, plane surface for the curved element/rail. In this connection, it may also be of interest to use angled module elements of a known type. The structure of the module elements will be dealt with in greater detail in the description which follows.

The feature which may chiefly be regarded as characterizing the new method for producing a bridge of the abovementioned type is that, among other things, a number of module units, corresponding to the number of dummies or attachment positions in the model, are selected from a module unit set which comprises module units with identical and/or differently designed surfaces which can cooperate with the elongate, flexible element or rail. The selected module units are oriented at an angle about the longitudinal axes common to them and to the implanted elements (dummies) in such a way that the module units come to support the elongate, flexible element or rail in a curved shape appropriate to each individual case. In addition, in the present invention the elongate, flexible element or rail is given its curved shape with the aid of a bending tool and the elongate, flexible element or rail once bent is secured in the module units for finishing the bridge.

The elongate, flexible element or rail is factory-made and is supplied in the form of a round bar of tissue-compatible material, preferably titanium, of a quality which, together with the profiling of the element or rail, permits bending without causing any essential deterioration of the strength characteristics of the element/frame in the bridge, joint, and the like. The profiling too is carried out at factory level and, seen in cross-section, comprises producing a plane bottom surface, making two lateral recesses for forming first and second lateral surfaces and a top part or ridge which in cross-section is slightly offset towards the first lateral surface, the latter forming an inside surface (innermost radius) in the curved shape of the elongate element or rail. The bar or profile can be extruded and cut to the correct length.

In one embodiment, those surfaces of the module elements cooperating with the flexible element/rail are worked in such a way that a common plane is formed, which essentially coincides with the plane of occlusion. The element or rail is fixed in the module elements preferably by means of welding, for example fillet welding. Connection holes to the implanted elements and/or to their parts are occupied and/or completed. The bridge is then covered with a coating, for example silicone, and if appropriate with composite.

In accordance with the present invention, it is possible to produce titanium bridges, or bridges made of another hard material, composite, and the like, without any risk of the bridge construction being unduly weakened from the stability point of view, and even though bending principle is used for the element/rail. The proposed construction also makes it possible to reliably secure a prosthesis part, for example tooth/tooth part, support part and the like. The securing means used is profiled to give stress-relieving edges and stress-relieving surfaces which considerably strengthen the attachment. The method for producing the titanium bridge is also facilitated by the fact that the shape of the flexible element/rail can be curved and that adapted during working, and it is also possible to carry out subsequent adjustments.

A presently proposed embodiment of a bridge system and a method having the features characteristic of the present invention will be described hereinbelow with reference to the attached drawings, in which

DETAILED DESCRIPTION OF THE PREFERRED EMBODIMENT

Figure 1:
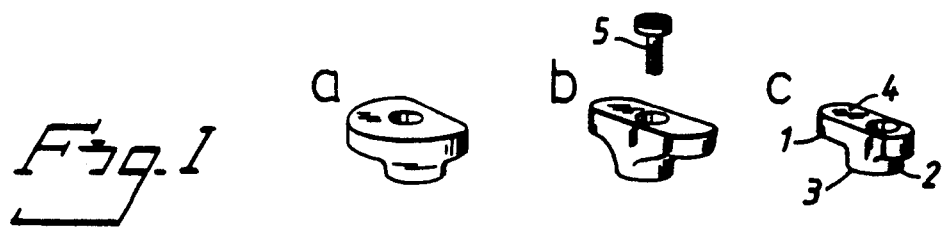
FIGS. 1a–1e show, in perspective and outline, a number of different module units which can be used.

FIG. 1 shows a number of differently designed module units a–e included in a module unit set or module unit sets for constructing dental bridges made of titanium or another hard material. Each module unit has a first section 1 and a second section 2. The second section has a securing part, by means of which the module unit can be secured in an implanted element or to a part fixed in such an implanted element. The securing part comprises a bearing surface 3. The first section has a further surface 4 which is separate from the bearing surface 3. FIG. 1b shows a screw 5 (gold) for screwing the module unit firmly into the implanted element or part belonging thereto. The section 2 can also be regarded as a spacing member integral with the module unit and distancing it from the said implant. FIG. 1d shows a longitudinal axis 6 about which the module unit can be oriented in different rotational positions positions. In FIG. 1d the module unit is oriented along the axis 7, but it can be turned in relation to this axis by an angle α.

Figure 2:
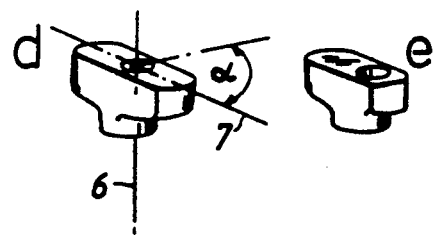
FIG. 2 shows, in a horizontal view, a number of curved shapes which the flexible element can assume.
Figure 2:
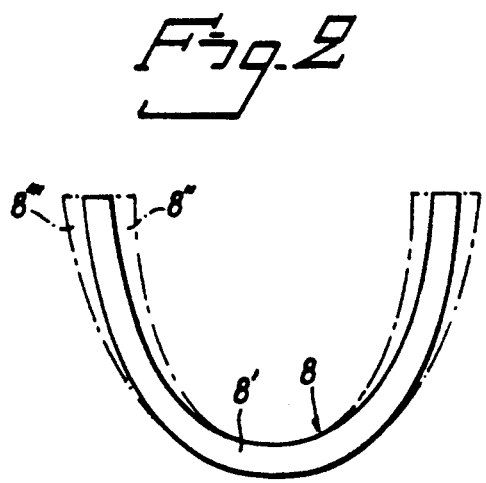

FIG. 2 shows an elongate, flexible element 8 in its curved shape. The element can be given a number of different curved shapes, and a first curved shape 8' is shown with full lines. Two additional curved shapes are illustrated by 8" and 8'''.

Figure 3:
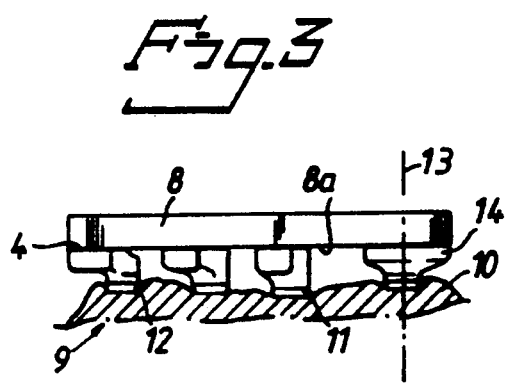
FIG. 3 shows a front view of a dentine model on which a bridge made up of module units and a flexible rail has been arranged.

In FIG. 3 a line of dentine is copied using a model 9, which has part 10 corresponding to the dentine. Dummies for elements implanted in the dentine are indicated by 11, 12. The dummies, or the attachment points which these represent, have positions and inclinations in the dentine corresponding to those of the implanted elements in the patient's jaw. The inclinations and positions can vary greatly from one individual to the next. With a comparatively small number of module elements, it should be possible to produce bridges covering a very large number of individuals. The shape of the module units and their rotatability about each respective longitudinal axis (6 in FIG. 1d) is therefore the key to this possibility. The module units according to FIG.

1 are selected from the actual set or sets. The further surfaces of the module units (FIG. 1c) are worked, for example by surface grinding, so that a common plane is obtained by the end surfaces or the surfaces 3 being bevelled. This common plane coincides with the underside 8a of the rail 8. The axis 13 is an axis common to an implanted element (which is not inclined) and a module unit 14. The further surface of the module unit 14 (see FIG. 1c) in this case needs to be bevelled in relation to the attachment section 2 (see FIG. 1c). The end surface need only be worked, if necessary, in height. The module element is thus arranged with different heights as regards the first section. In the case where the implanted element or its associated part is inclined in relation to the plane 8a, the further surface 4 is ground so that the common plane for the further surfaces can be obtained.

Figure 4:
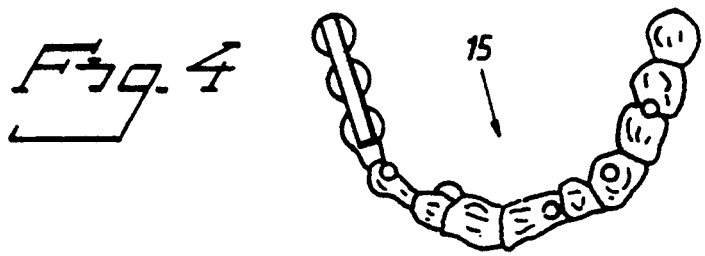
FIG. 4 shows, in a horizontal view, firmly welded retention elements in a composite-coated construction according to FIG. 3.
Figure 5:
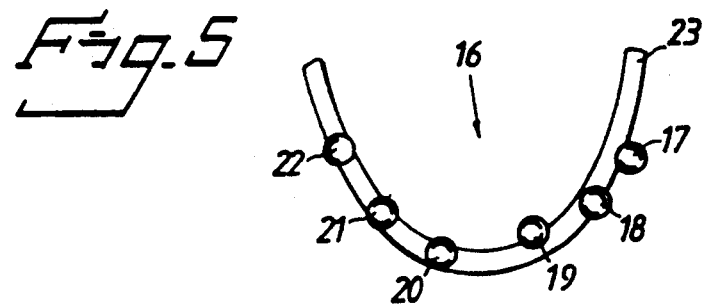
FIG. 5 shows, in a horizontal view, a bridge produced in a manner similar to that shown in FIG. 3.

By choosing suitable module units, it is possible to obtain an essentially common plane which coincides with the plane of occlusion. In an alternative or complementary embodiment, the end surfaces 3 of the second section 2 are bevelled, see FIG. 1c. By working the surfaces 3, a smaller amount of material need be worked. With the module elements fitted in this way and with the second surfaces in the same plane, a suitable curvature is chosen for the flexible element/rail 8. The element or rail is welded by fillet welding to the module units at the further surfaces 4. After welding, residual material is removed. Any connection holes for screws (5 in FIG. 1b) are filled or completed so that the bridge construction can be screwed into the implanted element. The residual material is removed. If appropriate, retention elements can be welded on. The construction is covered with a coating of silicone and is provided with composite. FIG. 4 is intended to show a composite-coated titanium bridge with welded retention elements at 15. FIG. 5 shows a welded metal construction 16 produced in accordance with the above. This figure shows how attachment points 17, 18, 19, 20, 21 and 22, that is the positions of the implanted elements, can be arranged outside or more or less within the chosen shape of the curvature of the rail 23. The above provides for a simplified method of producing a continuous beam (bridge) of high strength. By means of the present invention it is possible to position the rail/beam optimally for the best possible support from the module units. The fit can be extremely precise, for example 1/100 mm.

Figure 6:
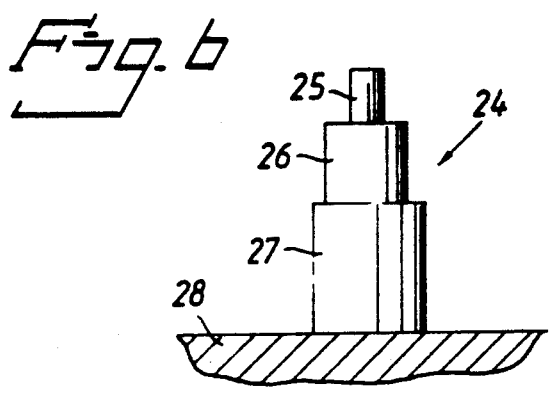
FIG. 6 shows from the side an example of a bending tool.

FIG. 6 shows a bending tool 24 which can be used to give the elongate, flexible element 8 according to FIG. 2 its final shape. The tool comprises in principle a number (for example 3) of cylindrical parts 25, 26 and 27. The cylindrical parts are fixed in a base unit 28 which can be clamped in a holding tool (for example a screw vice) which is not shown here.

Figure 7:
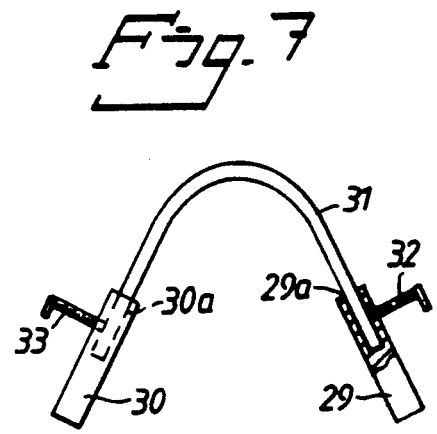
FIG. 7 shows, in a horizontal view, grip parts applied to the ends of the element in order to permit bending of the element with the aid of the tool illustrated in FIG. 6.

FIG. 7 shows grip parts 29, 30 which are included in the tool arrangement and which can be secured to the ends of the elongate, flexible element 31. The grip parts can have front recesses 29a, 30a which can be engaged on the said ends of the element or rail 31. In addition, there are securing members 32 and 33, by means of which the grips can be secured in the rail. The members 32, 33 can be of the screw type and can consist of screws cooperating with a thread in a hole in each grip part 29, 30. The ends of the screw thus cooperate with the rail upon tightening.

Figure 8:
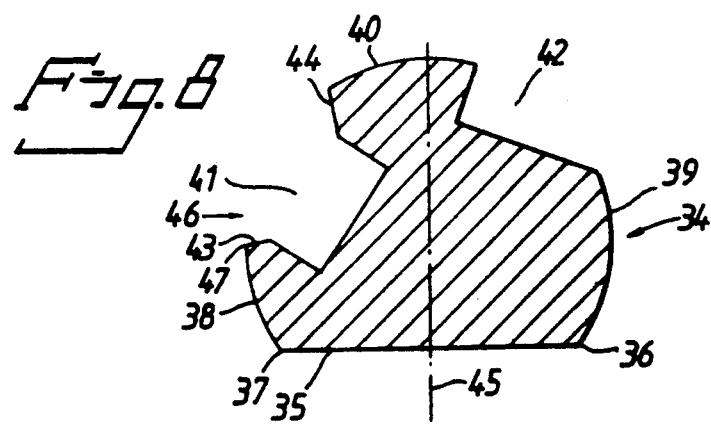
FIG. 8 shows, in cross-section, the profile of the flexible element/rail.

FIG. 8 shows an embodiment of an elongate, flexible element or rail 34. The rail is made of titanium, and the material has the quality designation TICPT (atomic number 22). The material has a modulus of elasticity in the range of 100–120. The modulus of elasticity is preferably about 110. Other material data of importance are a hardness of about 160 Vicker, a ductility of about 20%, a yield limit of about 25–45 kp/mm$^2$, and a breaking strength of about 35–49 kp/mm$^2$. In one embodiment the melt point is 1,688° C. The specific weight is about 4.5. The element/rail 34 is supplied in bar-shaped parts of predetermined length. The length is in this case such that it is sufficient to produce one bridge. FIG. 8 shows the bar in cross-section, and the bar extends at right angles to the plane of the paper. The cross-section or profile comprises a plane bottom surface 35. At points 36 and 37 the plane surface merges into first and second lateral parts 38 and 39. The first lateral part 38 has a longitudinal extent which is less than the longitudinal extent of the second lateral part 39. In one exemplary embodiment of the first lateral part is approximately half the length of the second lateral part. The lateral parts merge into a top part 40 via two recesses 41, 42. The starting material is a round bar, which means that the lateral parts 38 and 39 lie on the same circumference as the top part 40. In the recess 41 there are bevelled edges 43, 44 at the points of transition to the first lateral surface and the top part. The recess 41 is essentially square. The recess 42 cuts into the material without bevels corresponding to the bevels 43, 44. The cut-in from the lateral surface 39 is substantially greater than the cut-in from the top part 40. The cuts form essentially a right-angle in cross-section. The recesses 41 and 42 are also designed in such a way that the top part 40 has an asymmetrical position in relation to a perpendicular 45 through the bottom surface 35. The top part is in this way slightly offset towards the point 37 compared to the point 36. An inner radius for the curved shape of the rail is formed at the lateral surface 38, cf the arrow 46. The curving takes place around the diameter 47. By means of the choice of material and the profiling of the bar-shaped element or rail according to FIG. 8, the element/rail in its curved shape is able to maintain to a substantial extent its technical strength properties. During bending, the bottom surface 35 remains essentially plane, so that a good bearing is obtained against the top surfaces of the module elements.

Figure 9:
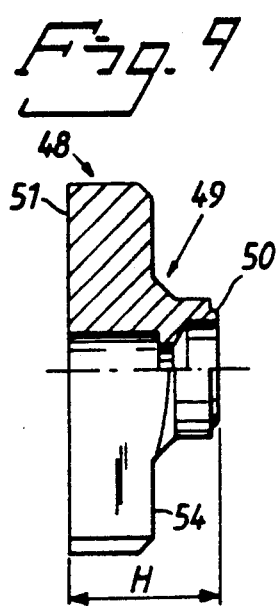
FIG. 9–17a show nine different constructions of the module units.
Figure 9A:
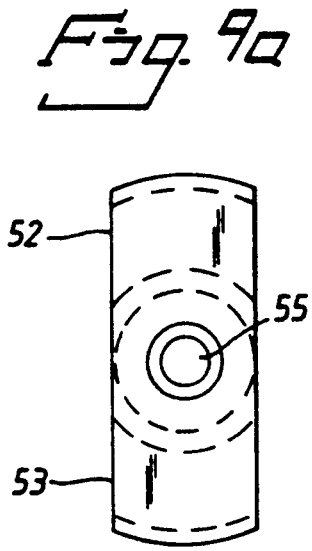
Figure 10:
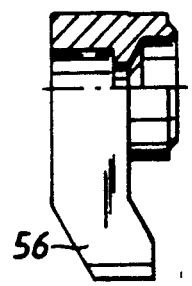
Figure 10A:
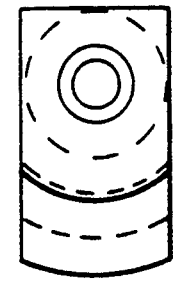
Figure 11:
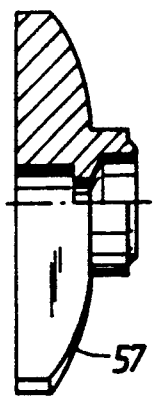
Figure 11A:
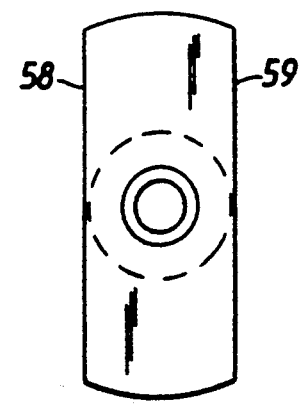
Figure 12:
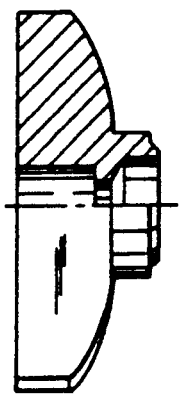
Figure 12A:
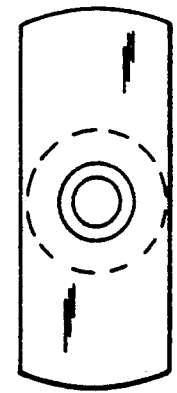
Figure 13:
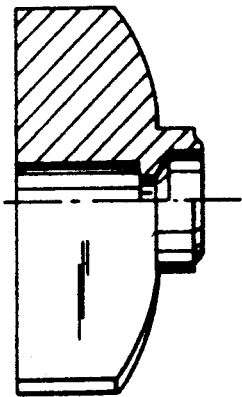
Figure 13A:
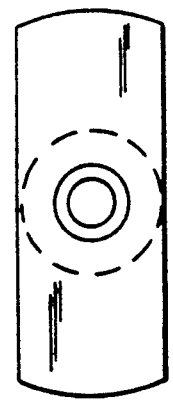
Figure 14:
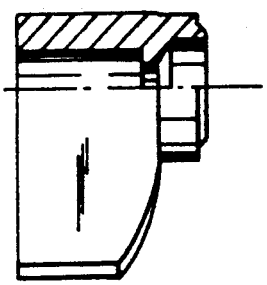
Figure 14A:
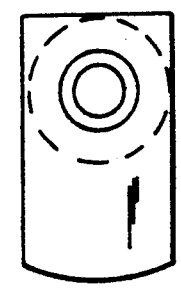
Figure 15:
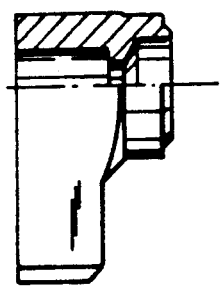
Figure 15A:
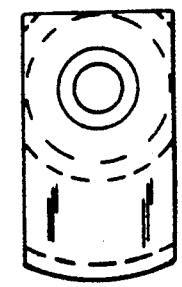
Figure 16:
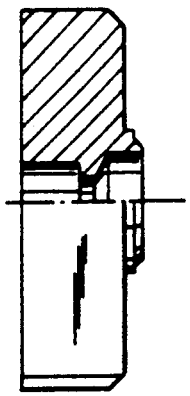
Figure 16A:
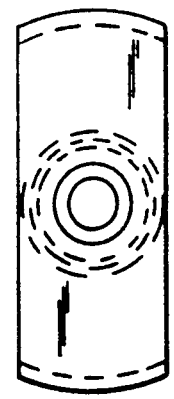
Figure 17:
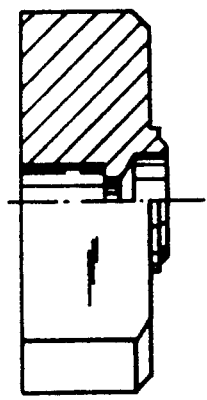
Figure 17A:
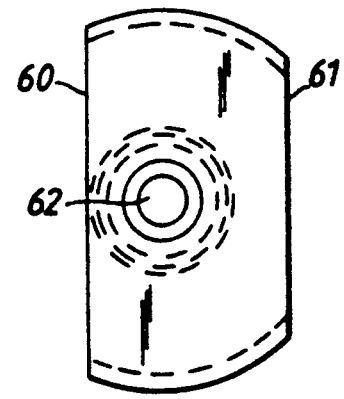

FIGS. 9–17a show nine different variants of the module units. In FIG. 9 the first and second sections are indicated by 48 and 49, respectively. In this case, the second section has the shape of a neck. The surface bearing against the implanted element or its part is indicated by 50. This bearing surface is formed with great dimensional accuracy, for example 1/100 mm. The further surface is indicated by 51. The further surface extends in this case over two wing-shaped parts 52, 53. The bottom surface 54 is essentially straight, and the module has a height H of a first dimension (for example 5 mm). A hole 55 for a retention screw is positioned in the middle of the surface 51. In the embodiment according to FIGS. 10, 10a the one wing-shaped part (cf parts 52, 53 in FIG. 9a) is in principle omitted. The remaining wing-shaped section is provided with a down-turned outer edge 56. The height (see H in FIG. 9) is slightly lower in this case. The embodiment according to FIGS. 11, 11a differs essentially from the embodiment according to FIGS. 9 and 9a in that the bottom surfaces 57 from the neck-shaped second section are curved upwards/outwards. The module units are also characterized by two essentially parallel lateral surfaces 58, 59 which are essentially common to all module units. The height H in the embodiment according to FIGS. 11, 11a is essentially the same as in the embodiment according to FIGS. 10, 10a. The embodiment according to FIGS. 12, 12a differs from the embodiment according to FIGS. 11, 11a in that the first section has a greater height, which means that the height of the module unit as a whole exceeds the height of the embodiment according to FIGS. 11, 11a. The embodiment according to FIGS. 13, 13a has an even greater height than the embodiment according to FIGS. 12, 12a. In other respects, the embodiments in question correspond. The embodiment according to FIGS. 14, 14a has the same height as the embodiment according to FIGS. 13, 13a but differs from the last-mentioned embodiment in that one ring is in omitted. Similar differences exist between the embodiments according to FIGS. 15, 15a and FIGS. 9, 9a. In the embodiment according to FIGS. 16, 16a the neck-shaped second section is substantially shortened in relation to the embodiment according to FIGS. 9, 9a. In the embodiment according to FIGS. 17, 17a the lateral surfaces 60, 61 have been displaced in relation to the recess 62 for the retention screw.

Figure 18:
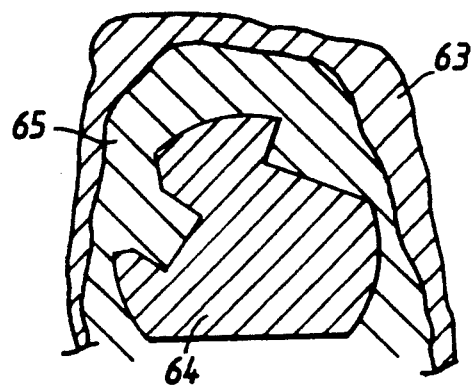
FIG. 18 shows, in a vertical section, a prosthesis part secured with retention means to the flexible element/rail.

FIG. 18 shows how a prosthesis part 63 in the form of a tooth, tooth part, cup, and the like can be anchored to the flexible element/rail 64 using retention means 65 in the form of acrylic, methyl acrylate, composite, plastic/resin, GMA, and the like.

The invention is not limited to embodiment illustrated hereinabove, but can be modified within the scope of the inventive concept and the patent claims which follow.

I claim:

1. A bridge system which is individually adapted to elements implanted in dentine, joints, or the like and/or to parts secured in the implanted elements, said bridge system comprising at least two module units which are attachable to the implanted elements or parts and have first surfaces for attachment to the elements and second surfaces separate from the first surfaces, and an elongate, curved member which is securable in the module units at said second surfaces, said elongate, curved member being designated with a profile and made of a material having a quality of titanium and a tissue affinity equivalent to that of titanium, said profile being designed in a cross-section with a plane underside adapted to be applied against said second surfaces and with means projecting from said underside to facilitate holding of a prosthesis part (tooth/tooth part), abutment or the like which is being secured in the bridge, said material and said profile permitting bending without essentially impairing the strength of the elongate element in the bridge.

2. A bridge system according to claim 1, wherein said projecting holding means includes two curved lateral parts which via recesses merge into a top part and wherein a first lateral part has a length which is less than that of a second lateral part, and wherein the recesses are designed so that the top part in the cross-section of the profile is positioned asymmetrical relative to a perpendicular through the center of said plane underside and is displaced slightly closer to a corner between said plane underside and a first lateral surface than to a corner between the plane underside and a second lateral surface, said elongate member being bendable so that the first lateral surface extends along and forms an inner radius as the elongate, curved member is given a curvature to follow the positions of the module units in the dentine, joint, and the like.

3. A bridge system according to claim 2, wherein the length of said first lateral part is half the length of the second lateral part.

4. A bridge system according to claim 3, wherein the recesses in the cross-section form anchoring steps for a plastic composite defining a retention means for holding the prosthesis part, in the bridge system.

5. A bridge system according to claim 1, wherein said material is titanium material having a modules of elasticity in the range of 100-120.

6. A bridge system according to claim 1, wherein about 5 to 15 different module units, each module unit having a securing part for securing the module unit in one of said implanted elements and a part which is separate from the securing part and which has one of said second surfaces and wherein a first section of the module unit bearing the second surface is widened in relation to a second section bearing the securing part on the module unit.

7. A bridge system according to claim 6, wherein at least one module unit has a second surface which is unique in relation to the second surfaces of the other module units, wherein the first and second sections on each module unit are designed to permit an at least essentially free orientation of the second surface around the longitudinal axis of the module unit, which coincides with the longitudinal axis of the implanted element, and thus permit an adaption to a desired curved shape of the elongate, curved member despite the fact that the implanted elements have positions in the dentine which differ from the desired shape.

8. A bridge system according to claim 1, wherein each module unit is designed with substantially parallel lateral surfaces.

9. A method of producing an individually adapted bridge using models of the dentine, jaw, joint, and the like, having dummies or attachment positions for elements implanted in the dentine, jaw, joint, and/or parts secured to the implanted elements, said method including the steps of:

providing a set of module units with at least two module units to be secured in the implanted elements and an elongate, flexible member to be secured in the module units to form a common plane for a prosthesis part;

selecting a number of module units corresponding to the number of dummies or attachments positions, from said set of module units said module units having designed surfaces adapted to cooperate with the elongate, flexible member; orienting the selected module units at an angle about the longitudinal axes common to them and to the implanted elements such that the module units support the elongate, flexible member in a curved shape suitable for each individual case;

effecting said curved shape for the elongate, flexible member with the aid of a bending tool; and securing the elongate, flexible member, once bent, in the module elements to complete the bridge;

wherein said elongate flexible member is made of tissue-compatible material, of a quality of titanium which, together with profiling of the curved elongate member permits bending without causing any essential deterioration of the strength properties of the elongate member in the bridge.

10. A method according to claim 9 wherein said profiling comprises, seen in cross-section, a plane bottom surface which is formed to extend uniformly in the longitudinal direction of the member, and two lateral recesses which extend in the longitudinal direction of the member to form first and second lateral surfaces and a top part which in cross-section is slightly displaced towards the first lateral surface which forms, at a corner, an inside surface with a minimum radius in the curved shape of the elongate member.

11. A method according to claim 10 wherein said module units include surfaces cooperating with said elongate flexible member which are worked and wherein those surfaces of the module units cooperating with the implanted elements or their parts are worked, so that a common plane is formed which essentially conincides with the plane of occlusion.

12. A method according to claim 11 wherein the elongate, flexible curved member is welded to the module units, wherein connection holes to the implanted elements are filled and wherein the bridge is covered with a coating.

13. A method according to claim 12, wherein said coating is a silicone coating.

* * * * *